United States Patent
Knauf et al.

(10) Patent No.: US 9,260,377 B2
(45) Date of Patent: Feb. 16, 2016

(54) METHOD FOR PRODUCING NITROBENZENE BY ADIABATIC NITRIDING

(71) Applicant: Bayer MaterialScience AG, Leverkusen (DE)

(72) Inventors: Thomas Knauf, Dormagen (DE); Michael Merkel, Dusseldorf (DE); Antoni Mairata, Dusseldorf (DE)

(73) Assignee: Bayer MaterialScience AG, Leverkusen (DE)

( * ) Notice: Subject to any disclaimer, the term of this patent is extended or adjusted under 35 U.S.C. 154(b) by 0 days.

(21) Appl. No.: 14/415,788

(22) PCT Filed: Jul. 23, 2013

(86) PCT No.: PCT/EP2013/065504
§ 371 (c)(1),
(2) Date: Jan. 20, 2015

(87) PCT Pub. No.: WO2014/016290
PCT Pub. Date: Jan. 30, 2014

(65) Prior Publication Data
US 2015/0175522 A1 Jun. 25, 2015

(30) Foreign Application Priority Data
Jul. 27, 2012 (EP) .................................... 12178159

(51) Int. Cl.
*C07C 201/06* (2006.01)
*C07C 201/08* (2006.01)

(52) U.S. Cl.
CPC ............. *C07C 201/06* (2013.01); *C07C 201/08* (2013.01)

(58) Field of Classification Search
CPC ........................... C07C 201/06; C07C 201/08
USPC ...................................................... 568/939
See application file for complete search history.

(56) References Cited

U.S. PATENT DOCUMENTS

| 2,256,999 | A | | 9/1941 | Castner |
| 4,091,042 | A | | 5/1978 | Alexanderson et al. |
| 4,257,986 | A | * | 3/1981 | Milligan et al. ............... 568/934 |
| 5,313,009 | A | | 5/1994 | Guenkel et al. |
| 5,763,697 | A | | 6/1998 | Hermann et al. |
| 7,326,816 | B2 | | 2/2008 | Knauf et al. |
| 7,344,650 | B2 | | 3/2008 | Knauf et al. |
| 7,781,624 | B2 | | 8/2010 | Rausch et al. |
| 8,357,827 | B2 | | 1/2013 | Munnig et al. |
| 2011/0196177 | A1 | * | 8/2011 | Munnig et al. ................. 568/939 |
| 2013/0204043 | A1 | | 8/2013 | Knauf et al. |

FOREIGN PATENT DOCUMENTS

| DE | 102009005324 A1 | 7/2010 |
| EP | 0373966 A2 | 6/1990 |
| EP | 0436443 A2 | 7/1991 |
| EP | 0976718 A2 | 2/2000 |
| EP | 1132347 A2 | 9/2001 |
| WO | 2010051616 A1 | 5/2010 |

\* cited by examiner

*Primary Examiner* — Sikarl Witherspoon
(74) *Attorney, Agent, or Firm* — N. Denise Brown; Donald R. Palladino

(57) ABSTRACT

The invention provides a continuous adiabatic process for the preparation of nitrobenzene by nitrating benzene with mixtures of sulfuric and nitric acids using a stoichiometric excess of benzene, wherein the content of organic compounds in the circulating sulfuric acid, at least during the start-up period of the production plant, is always kept below 1.0 mass percent, based on the total mass of circulating sulfuric acid. This is preferably achieved by a procedure in which, either after the end or before the beginning of a production cycle, the circulating sulfuric acid is circulated at elevated temperature so that the organics contained in the sulfuric acid, preferably comprising nitrobenzene and traces of benzene, dinitrobenzene and nitrophenols, are separated off in the evaporation apparatus for concentrating the sulfuric acid.

14 Claims, 1 Drawing Sheet

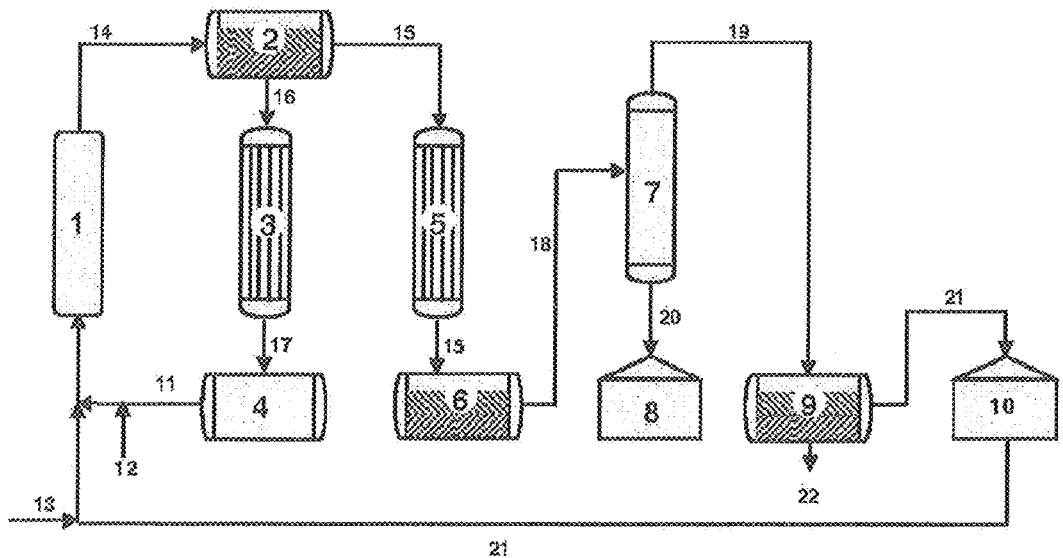

METHOD FOR PRODUCING NITROBENZENE BY ADIABATIC NITRIDING

CROSS-REFERENCE TO RELATED APPLICATIONS

This application is a National Phase Application of PCT/EP2013/065504, filed Jul. 23, 2013, which claims priority to European Application No.: 12178159.5, filed Jul. 27, 2012, each of which being incorporated herein by reference.

FIELD

The invention provides a continuous adiabatic process for the preparation of nitrobenzene by nitrating benzene with mixtures of sulfuric and nitric acids using a stoichiometric excess of benzene, wherein the content of organic compounds in the circulating sulfuric acid, at least during the start-up period of the production plant, is always kept below 1.0 mass percent, based on the total mass of circulating sulfuric acid. This is preferably achieved by a procedure in which, either after the end or before the beginning of a production cycle, the circulating sulfuric acid is circulated at elevated temperature so that the organics contained in the sulfuric acid, preferably comprising nitrobenzene and traces of benzene, dinitrobenzene and nitrophenols, are separated off in the evaporation apparatus for concentrating the sulfuric acid.

BACKGROUND

The present invention relates to a continuous process for the preparation of nitrobenzene by the adiabatic nitration of benzene with a mixture of sulfuric and nitric acids (so-called 'mixed acid'). Such a process was first claimed in U.S. Pat. No. 2,256,999 and is described in more modern embodiments in U.S. Pat. No. 4,091,042, U.S. Pat. No. 5,313,009 and U.S. Pat. No. 5,763,697.

A common feature of the adiabatic processes described is that the starting materials, benzene and nitric acid, are reacted in a large excess of sulfuric acid, which absorbs the heat of reaction evolved and the water formed in the reaction.

The reaction procedure generally involves combining the nitric acid and sulfuric acid to give so-called 'nitrating acid' (also called 'mixed acid'). Benzene is metered into this nitrating acid. The reaction products are essentially water and nitrobenzene. In the nitration reaction, benzene is used in at least the stoichiometric amount, but preferably in 2% to 10% excess, based on the molar amount of nitric acid. According to the state of the art, the crude nitrobenzene formed in the reaction apparatuses and separated from the acid phase in the phase separation apparatus is washed and worked up by distillation, as described e.g. in EP 1 816 117 A1 (page 2, lines 26 to 42), U.S. Pat. No. 4,091,042 (cf. above) or U.S. Pat. No. 5,763,697 (cf. above). A characteristic feature of this work-up is that, after washing, unreacted excess benzene is separated from nitrobenzene in a final distillation and re-used in the nitration reaction as recycle benzene, which also comprises low-boiling non-aromatic organic compounds (so-called 'low boilers') (cf. DE 10 2009 005 324 A1). The treatment of the exhaust gas from the adiabatic nitration reaction is described in EP 0 976 718 B1. The exhaust gas from the acid circuit and final crude nitrobenzene is drawn off, combined and passed through an $NO_x$ absorber to recover dilute nitric acid, which is returned to the reaction. The sulfuric acid, referred to as circulating acid, is concentrated in a flash evaporator and freed of organics as far as possible. High-boiling organics, e.g. nitrobenzene, dinitrobenzene and nitrophenols, and traces of benzene, remain in the circulating acid and are therefore also returned to the reaction.

When the exhaust gas from an adiabatic nitration reaction is worked up as described in EP 0 976 718 B1, i.e. when the exhaust gas from the acid circuit and final crude nitrobenzene is drawn off, combined and passed through an $NO_x$ absorber to recover dilute nitric acid, which is returned to the reaction, it is advisable not to return this dilute nitric acid to the reaction until the start-up process (meaning the period of time within which a production plant is brought to target load from shutdown; cf. below for details) has ended, because admixing of the dilute nitric acid reduces the overall concentration of the starting nitric acid and causes reaction kinetics to slow down.

The quality of an adiabatic process for the nitration of aromatic hydrocarbons is defined on the one hand by the content of unwanted reaction by-products in the product, which are formed by multiple nitration or oxidation of the aromatic hydrocarbon or the nitroaromatic. In the preparation of nitrobenzene one strives to minimize the content of dinitrobenzene and nitrophenols, particularly trinitrophenol (picric acid), which is classified as explosive. The quality of an adiabatic process is defined on the other hand by the fact that the process can be operated without a technical shutdown of production.

To obtain nitrobenzene with particularly high selectivities, the nature of the mixed acid to be used has been stipulated in detail (EP 0 373 966 B1, EP 0 436 443 B1 and EP 0 771 783 B1) and it has been pointed out that the content of by-products is determined by how high the maximum temperature is (EP 0 436 443 B1, column 15, lines 22 to 25). It is also known that a high initial conversion is advantageous for a high selectivity and that this is achieved if optimum mixing is applied at the beginning of the reaction (EP 0 771 783 B1, paragraph [0014]).

Outstanding selectivities are obtained when the chosen initial reaction temperature is very low (WO 2010/051616 A1), although this is tantamount to increasing the reaction time several fold. A high space-time yield is advantageous for the industrial application of a process, since this makes it possible to construct compact reaction equipment distinguished by low capital expenditure in relation to capacity. This approach is therefore counter-productive.

Common to all the literature references listed is the fact that they do not describe the start-up process of a nitration unit and its difficulties.

As regards the quality of the auxiliary material sulfuric acid in the adiabatic preparation of nitrobenzene, EP 2 070 907 A1 describes that low contents of metal ions in the sulfuric acid obtained from the nitration have a positive effect on the concentration of the sulfuric acid. Thus, in the flash evaporation (i.e. evaporation associated with expansion) of the waste acid comprising sulfuric acid, which is obtained after separation of the aqueous phase from the reaction mixture obtained from the nitration of benzene, higher sulfuric acid concentrations are achieved in the resulting concentrated sulfuric acid when the content of metal ions is low. This is probably attributable to the improved evaporability of the water in the flash evaporator when there are low contents of metal ions in the waste acid. It has thus been found that, in flash evaporation under otherwise identical conditions (same temperature of the waste acid, same sulfuric acid content of the waste acid, same pressure in the flash evaporator), the concentration of $H_2SO_4$ in the concentrated sulfuric acid obtained is up to 0.25% higher when using a waste acid with low contents of metal ions of less than 900 mg/l.

EP 2 070 907 A1 further describes that lower metal ion concentrations in the sulfuric acid also result in a lowering of the boiling point of the sulfuric acid, which in turn reduces the amount of energy required to concentrate the sulfuric acid.

EP 2 070 907 A1 further points out that the problematic deposits of metal sulfates can be found not only in heat exchangers but also at any points where the concentration of the metal ions that form hardly soluble metal sulfates is sufficiently high and the temperature sufficiently low to cause the formation of solids, and where at the same time the flow rate of the sulfuric acid or the cross-section of the sulfuric acid pipelines is sufficiently small to cause an accumulation of the metal sulfates that interferes with the process. Therefore, not only can metal sulfate deposits be observed in heat exchangers, but metal sulfates can also occur as deposits on the bottom of tanks, at measuring points like level measurings, and on dispersing elements, which conventionally have small flow orifices. Likewise, metal sulfate deposits can also occur inside the flash evaporators, where the sulfuric acid is conventionally cooled while water is evaporated and the concentration of the acid is increased. Moreover, deposits of metal salts can also form in the work-up steps following the reaction, e.g. in the effluent work-up, due to entrained metal sulfates. According to the state of the art cited above, necessary provision is made for a periodic cleaning of the affected parts of the plant in order to reduce the interference caused by these deposits. However, this cleaning entails production shutdowns and hence additional costs. The cleaning of heat exchangers and pipelines that convey sulfuric acid to remove solid precipitated metal sulfates can be dispensed with if, in the nitration of the benzene by a mixed acid comprising sulfuric and nitric acids, the sulfuric acid recovered by the flash evaporation of water is not completely recycled into the reaction zone as recycled acid, but partially removed and replaced by fresh sulfuric acid which is poor in metal ions.

EP 2 070 907 A1 does not go into organic compounds which can concentrate in the circulating sulfuric acid, above all when the production plant is operated at high loads.

It is true that the processes of the prior art described succeed in preparing a nitrobenzene having a low content of by-products, i.e. comprising only from about 100 ppm to 300 ppm of dinitrobenzene and 1500 ppm to 2500 ppm of nitrophenols, wherein picric acid can make up a proportion of 10 mass percent to 50 mass percent of the nitrophenols. The processes are also distinguished by a high space-time yield. However, only processes that are already in progress are described, i.e. processes in which the period from the beginning of the reaction until the target load is achieved (so-called 'start-up period') has already passed. Any particular difficulties during the start-up of an adiabatic nitration process are not mentioned.

BRIEF DESCRIPTION OF DRAWINGS

FIG. 1 is a flow diagram of a nitrobenzene in a production process according to the Examples.

DETAILED DESCRIPTION

The starting point for the present invention was the knowledge that impurities in the starting materials or auxiliary materials, especially impurities in the circulating sulfuric acid used, have a particularly adverse effect on the process during the start-up period.

Organic impurities such as nitrobenzene, dinitrobenzene and nitrophenols in the circulating sulfuric acid reduce the total available concentration of nitric acid. Although this does not slow the reaction down, the reduced nitric acid concentration can result in using too much benzene. This increases the energy consumption in the work-up of the crude nitrobenzene because this excess benzene has to be cooled down after the nitration and separated from nitrobenzene by distillation. Moreover, the additional benzene shortens the residence times in all the apparatuses, which slows down the initial reaction. There is also an increase in by-products because organic impurities like nitrobenzene are nitrated further with nitric acid.

Taking the above into account, the present invention provides a process for the preparation of nitrobenzene in which particular attention is paid to the critical period of the start-up of the reaction. In particular, it has been found that, by limiting the content of organic compounds in the circulating sulfuric acid, at least during the start-up period, the aforementioned difficulties are overcome or at least significantly reduced. This limiting of the content of organic compounds in the circulating sulfuric acid, at least during the start-up period, can be achieved in various ways, which are provided by the present invention.

In particular, the present invention provides a continuous process for the production of nitrobenzene by nitration of benzene, in which a) a benzene-containing stream (a.1), comprising preferably at least 90 mass percent, particularly preferably at least 95 mass percent and very particularly preferably at least 99 mass percent of benzene, based in each case on the total mass of (a.1), is reacted in a reactor with a mixture of sulfuric acid (a.2) and nitric acid (a.3) under adiabatic conditions, benzene being used in a stoichiometric excess, based on nitric acid (a.3) of preferably of 2.0% to 20%, particularly preferably of 5.0% to 10% of theory, and the quantity M' of the benzene-containing stream (a.1) supplied to the reactor per hour being increased within a period t from the beginning of the nitration until a preset target value for M' is achieved, b) the process product obtained in step a) is separated in a phase separation apparatus into an aqueous phase (b.1) comprising sulfuric acid and an organic phase (b.2) comprising nitrobenzene, c) the aqueous phase (b.1) obtained in step b) is concentrated by evaporation of water in an evaporation apparatus (so-called 'flash evaporator') to give an aqueous phase (c.1) comprising sulfuric acid and having a higher sulfuric acid concentration than (b.1), the phase (c.1) being recycled into step a) via a sulfuric acid tank and used as a component of (a.2), and d) the organic phase (b.2) obtained in step b) is worked up to pure nitrobenzene (d.1), preferably by washing with aqueous media and subsequent rectification, and in which, at least during the period of time t, only a sulfuric acid stream (a.2) having a content of organic compounds of less than 1.0 mass percent, preferably of less than 0.50 mass percent and particularly preferably of less than 0.20 mass percent, based in each case on the total mass of (a.2), is supplied to the reactor.

The benzene excess based on nitric acid of 2.0% to 20%, preferably of 5.0% to 10% of theory, refers to the molar ratio of benzene and nitric acid. Theoretically one mole of nitric acid reacts with one mole of benzene to form one mole of nitrobenzene.

The skilled artisan is aware that a continuous industrial process starting from a production plant that is not in operation (e.g. after a shutdown for maintenance) cannot instantly be restored to the process parameters from before the production shutdown. Starting materials and apparatuses have to be heated up, apparatuses may have to be rendered inert, and the load of the apparatuses with the starting materials is increased gradually to the desired target value. If a production plant for the production of nitrobenzene is to be operated at a target load $M'_{target}$ of x [kg(benzene)/h], this target load can be achieved e.g. by initially adjusting the load M' to a value of 0.25x at the beginning of the nitration and then increasing the load via the intermediate steps M'=0.50x and M'=0.75x over 4 hours up to the value M'=x=$M'_{target}$. Alternatively, the load can be increased continuously from a specific starting value, e.g. M'=0.50x, up to M'=x. Of course, these examples are only representative of a large number of possible start-up procedures, the precise arrangement of which depend on the actual conditions of a production plant and cannot therefore be generalized. However, a common feature of all putative start-up procedures is that the requisite target load of x is only reached after a period of time t has passed. This period of time t is referred to according to the invention as the start-up period. During the start-up period the mass flow of nitric acid (a.3) being continuously supplied to the reactor is, of course, matched to the respective mass flow of the benzene-containing stream (a.1), i.e. at the beginning of the start-up period, when only a fraction of the requisite target load of benzene $M'_{target}$ is supplied to the reactor, only a corresponding fraction of the nitric acid (a.3) is also supplied to the reactor. Preferably, the percentage excess of benzene, based on nitric acid, is kept the same during the start-up period t as after reaching the target load $M'_{target}$. During the start-up period the mass ratio of nitric acid (a.3) to sulfuric acid (a.2) can differ from the ratio after reaching the target load of benzene, $M'_{target}$; in particular, it can be lower. In particular, it is preferred to supply only sulfuric acid (a.2) to the reactor initially and to supply nitric acid (a.3) and benzene-containing stream (a.1) only after reaching a stable operating state of the sulfuric acid circuit.

According to the invention, nitric acid is used in a substoichiometric amount, so that the aqueous part (b.1) of the crude reaction product obtained in step a) consists essentially of dilute sulfuric acid, which is concentrated in step c) to enable the sulfuric acid to be recycled. In general, it is possible to recycle all the sulfuric acid, so the addition of fresh sulfuric acid in step a) can be largely or completely dispensed with, meaning that the sulfuric acid stream (a.2) preferably corresponds to the recycled sulfuric acid stream (c.1), the so called 'circulating sulfuric acid stream', because it is used repeatedly and hence is circulated during the reaction. When necessary, sulfuric acid losses are replenished by the appropriate addition of fresh sulfuric acid in step a). The sulfuric acid stream (a.2) is thus composed of circulating sulfuric acid (c.1) and, if applicable, added fresh sulfuric acid. Preferably, the sulfuric acid (a.2) comprises 95 mass percent to 100 mass percent of concentrated sulfuric acid (c.1), based on the total mass of (a.2). Fresh sulfuric acid is normally free of organic compounds, so attention should be focused on the circulating sulfuric acid (c.1) in the context of the present invention. This circulating sulfuric acid accumulates organic compounds during operation. According to present knowledge from the state of the art, this should not be a problem because the sulfuric acid comes into contact anyway with organic compounds, namely the starting material benzene and, after the conversion has started, the product nitrobenzene. However, as illustrated in greater detail below, it has surprisingly been found within the framework of the present invention that positive effects are obtained by limiting the content of organics in the circulating sulfuric acid.

Organic compounds within the meaning of the present invention are preferably selected from the group consisting of benzene, nitrobenzene, the isomers of dinitrobenzene and the isomers of nitrophenol, nitrobenzene being particularly preferred. According to the invention, the content of organic compounds in the circulating sulfuric acid must be monitored. Analytical measurements are required for this purpose. The circulating sulfuric acid in the buffer tank to reaction is measured, preferably by taking samples at appropriate places and analysing them by gas chromatography. Other analytical methods (e.g. spectroscopic methods), where appropriate also online or inline, can, although not preferred, be used in principle. Prevailing for the upper limit of the content of organic compounds according to the invention, however, is the determination by gas chromatography.

The word "a/an" within the framework of this invention in connection with countable parameters is to be understood as an indication of number only if this is expressly stated. For example, the expression "a reactor" does not exclude the possibility of the presence of several reactors (connected in series or in parallel).

It is essential to the invention that the content of organic compounds—especially nitrobenzene—in the sulfuric acid-containing stream (a.2) corresponds to the above-mentioned concentrations at least during the start-up period t. This goal can be achieved in alternative ways:

In a first variant, after the end of a production cycle, i.e. after the end of benzene (a.1) and nitric acid (a.3) addition and complete conversion to nitrobenzene of the remainders still present in the production plant, a phase separation is carried out in a phase separation apparatus and the organic phase, comprising benzene, nitrobenzene and organic by-products, is removed therefrom. This minimizes the absolute amount of organics to be removed in the evaporation apparatus, and none of the organics, other than those dissolved in the circulating acid, passes through the evaporation apparatus into the sulfuric acid tank. The remaining concentrated sulfuric acid (c.1) is then circulated through the reactor, the phase separation apparatus, the evaporation apparatus and the sulfuric acid tank at elevated temperature, preferably at a temperature of 60° C. to 140° C., particularly preferably at 100° C. to 140° C., with the absolute pressure in the evaporation apparatus, after shutting down the reaction, preferably being adjusted to 50 mbar to 300 mbar, particularly preferably 70 mbar to 100 mbar and very particularly preferably 80 mbar to 90 mbar, until the required maximum content of organic compounds in the circulating sulfuric acid stream (c.1) of less than 1.0 mass percent, preferably of less than 0.50 mass percent and particularly preferably of less than 0.20 mass percent, based in each case on the total mass of the circulating sulfuric acid (c.1), is reached. The organic compounds pass into the gas phase and are withdrawn from the evaporation apparatus. To promote the removal of the organic compounds, especially nitrobenzene, from the circulating sulfuric acid (c.1), small amounts of water (preferably 0.1 mass percent to 2 mass percent, based on the total mass of the circulating sulfuric acid (c.1)) can be added to said sulfuric acid. The water used here is preferably demineralized water, particularly preferably a mixture of demineralized water and vapour condensate (i.e. a condensate of water vapour which has been obtained by heat exchange between water and any exothermic process steps) and very particularly preferably vapour condensate. When the reaction is started up again, sulfuric acid (c.1) out of the sulfuric acid tank is fed into the reactor as stream (a.2), optionally after addition of fresh sulfuric acid. As fresh sulfuric acid comprises either no organic compounds at all or only insignificant traces, this ensures that the requirements according to the invention regarding the maximum content of organic compounds in stream (a.2) are kept for a sufficiently long time, i.e. at least during the start-up period. The invention therefore also provides in particular a process in which the continuous reaction is interrupted by stopping the addition of benzene-containing stream (a.1) and nitric acid (a.3) and, after complete conversion of residual nitric acid present in the reactor to nitrobenzene, after removal of the organic phase (b.2) from the phase separation apparatus and after concentrating (b.1) to (c.1), the remaining sulfuric acid-containing phase (c.1) is circulated through the reactor, the phase separation apparatus, the evaporation apparatus and the sulfuric acid tank at a temperature of 60° C. to 140° C., preferably at 100° C. to 140° C., with the absolute pressure in the evaporation apparatus preferably being adjusted to 50 mbar to 300 mbar, particularly preferably 70 mbar to 100 mbar and very particularly preferably 80 mbar to 90 mbar, until the content of organic compounds in (c.1) is less than 1.0 mass percent, preferably less than 0.50 mass percent and particularly preferably less than 0.20 mass percent, based in each case on the total mass of the sulfuric acid-containing phase (c.1), and in which the so purified sulfuric acid-containing phase (c.1) is used as a component of (a.2) in the next production cycle.

In a second variant, before starting a new production cycle, i.e. before addition of benzene (a.1) and nitric acid (a.3), the concentrated sulfuric acid (c.1) still remaining from the last production cycle is circulated through the reactor, the phase separation apparatus, the evaporation apparatus and the sulfuric acid tank at elevated temperature, preferably at a temperature of 60° C. to 140° C., particularly preferably at a temperature of 80° C. to 120° C. and very particularly preferably at 90° C. to 110° C., with the absolute pressure in the evaporation apparatus preferably being adjusted to 50 mbar to 300 mbar, particularly preferably 70 mbar to 100 mbar and very particularly preferably 80 mbar to 90 mbar, until the required maximum content of organic compounds in the circulating sulfuric acid stream (c.1) of less than 1.0 mass percent, preferably of less than 0.50 mass percent and particularly preferably of less than 0.20 mass percent, based in each case on the total mass of the circulating sulfuric acid (c.1), is reached. The organic compounds pass into the gas phase and are withdrawn from the evaporation apparatus. When the reaction is started up again, the sulfuric acid (c.1) of the sulfuric acid tank is then fed into the reactor as the stream (a.2), optionally after the addition of fresh sulfuric acid. As fresh sulfuric acid comprises either no organic compounds at all or only insignificant traces, this ensures that the requirements according to the invention regarding the maximum content of organic compounds in stream (a.2) are kept for a sufficiently long time, i.e. at least during the start-up period. The invention therefore also provides in particular a process in which, starting from a production plant that is not in operation before the start of a new production cycle, i.e. before the beginning of the addition of benzene-containing stream (a.1) and nitric acid (a.3), the sulfuric acid-containing phase (c.1) which is still there from the previous production cycle is circulated through the reactor, the phase separation apparatus, the evaporation apparatus and the sulfuric acid tank at a temperature of 60° C. to 140° C., preferably at 80° C. to 120° C. and particularly preferably at 90° C. to 110° C., until the content of organic compounds in (c.1) is less than 1.0 mass percent, preferably less than 0.50 mass percent and particularly preferably less than 0.20 mass percent, based in each case on the total mass of the sulfuric acid-containing phase (c.1), and in which the so purified sulfuric acid-containing phase (c.1) is used as a component of (a.2) in the new production cycle.

Therefore the two variants differ in the point in time at which the circulating sulfuric acid is pumped through the circuit at elevated temperature ('decocted'). The second variant is preferably used in the event of an unscheduled shutdown of the nitration unit. The two variants can also be combined.

Steps a) to d) of the invention are now illustrated in greater detail below. Different embodiments can be freely combined with one another so long as those skilled in the art do not perceive an obvious contradiction in the context.

In principle, step a) can be carried out by any of the adiabatic nitration processes known from the state of the art, provided that the specified boundary conditions regarding the benzene excess and the purity of starting materials and auxiliary materials can be maintained. This step of the process according to the invention is preferably executed using a tubular reactor in which several dispersing elements are distributed over the length of the reactor, which ensures thorough dispersion and mixing of benzene, nitric acid and sulfuric acid. Such a reactor, and the shape of dispersing elements which can be used, are described e.g. in EP 0 708 076 B1 (FIG. 2) and EP 1 291 078 A2 (FIG. 1). Step a) is preferably executed by a process operation such as that described in DE 10 2008 048 713 A1, especially paragraph[0024].

The phase separation in step b) also takes place according to prior art in processes known per se in a separation tank familiar to the skilled artisan. The aqueous phase (b.1) comprises essentially (as a result of the formation of water of reaction and by the entrainment of water into the reaction from the nitric acid used) dilute sulfuric acid together with inorganic impurities; the organic phase (b.2) comprises essentially nitrobenzene together with excess benzene and organic impurities.

In principle, the concentrating of the aqueous phase (b.1) in step c) takes place as known from prior art. The sulfuric acid in the aqueous phase is concentrated in a flash evaporator by evaporating water into a range of reduced pressure. If the reaction conditions in the adiabatic nitration of benzene with mixed acid are chosen correctly, the heat of the exothermic reaction heats the aqueous phase (b.1) comprising sulfuric acid to a sufficient extent that the concentration and temperature of the aqueous phase comprising sulfuric acid in the flash evaporator can simultaneously be re-established to the concentration and temperature of said phase which it had on entering the reaction space prior to the reaction with benzene and nitric acid, i.e. (c.1) corresponds to (a.2) in terms of temperature and concentration. This is described in EP 2 354 117 A1, especially paragraph[0045].

The work-up of the organic phase (b.2) in step d) takes place in principle as known from prior art. A preferred procedure is described below:

The organic phase (b.2), which usually still comprises traces of acid, is washed in one or two washes, preferably one wash, with an aqueous washing liquid and then separated from the acidic aqueous phase by phase separation (in the case of several washes, after each individual wash). The acid residues contained in the crude nitrobenzene (b.2) are washed out in this process, so this process step is also referred to as an acid wash. This step is sufficiently well known from the state of the art and is therefore only briefly outlined here. Preferably, aqueous streams obtained during operation are recycled for the purpose of carrying out this acid wash. (step d(i))

The resulting organic phase is then washed in one to two, preferably one, alkaline wash(es), with an aqueous solution of a base preferably selected from the group consisting of sodium hydroxide, sodium carbonate and sodium hydrogen carbonate, and then separated from the alkaline washing water by phase separation (in the case of several washes, after each individual wash). Particularly preferably, sodium hydroxide solution is used as the aqueous base solution. This step is sufficiently well known from the state of the art and is therefore only briefly outlined here. The pH of the sodium hydroxide solution used and its mass ratio to the organic phase are adjusted so that acidic impurities (e.g. nitrophenols formed as by-products and acid residues not completely removed in step b)) are largely to fully neutralized, preferably fully neutralized, in step c). The subsequent work-up of the alkaline waste water can take place by processes of the prior art, e.g. according to EP 1 593 654 A1 and EP 1 132 347 A2. (step d(ii))

Finally, the resulting organic phase is washed with water in at least one, preferably two to four, particularly preferably two to three and very particularly preferably two neutral wash(es), and then separated from the aqueous phase by phase separation (in the case of several washes, after each individual wash). In principle, this can be carried out by any of the methods conventionally used in the state of the art. The washing water used here is preferably deionized water (DI water), particularly preferably a mixture of DI water and steam condensate (i.e. a condensate of water vapour which was obtained by heat exchange between water and any exothermic process steps) and very particularly preferably steam condensate. A preferred procedure is one in which electrophoresis is employed in the last neutral wash (cf. WO 2012/013678 A2). (step d(iii))

The washed nitrobenzene is finally freed from dissolved water, unreacted benzene and if so organic impurities by further work-up. This work-up is preferably carried out by distillation, the vapours of water, benzene and if so organic impurities being expelled overhead. The vapours are cooled and led into a separation tank. Water settles out in the lower phase and is separated off. The upper phase comprises benzene and low boilers, which are supplied back to the reaction as recycle benzene (d.2). A rectification column is preferably used as the distillation apparatus. The bottom product of the distillation is, optionally after a further distillation in which nitrobenzene is obtained as distillate (i.e. as top or side stream product), supplied as pure nitrobenzene (d.1) to other purposes (such as hydrogenation to aniline). (step d(iv))

By means of the approaches according to the invention, the following advantages are obtained for the start-up procedures of adiabatic nitration:
i) The reaction mixture heats up more quickly because the organic impurities in the recycled sulfuric acid do not have to be heated up as well. The use of steam to assist the reaction can therefore be dispensed with earlier.
ii) The benzene conversions are optimal and only the amount of benzene in excess of the theoretical amount, and not additional benzene present due to an incomplete reaction, burdens the work-up in step d).
iii) The formation of by-products in the reaction such as dinitrobenzene and picric acid is minimized because, between the metering of nitric acid and the metering of benzene at the reactor inlet, there is not a significant amount of nitrobenzene that could undergo secondary reactions with the large excess of nitric acid present at said inlet.
iv) The absence of organic impurities in the circulating sulfuric acid when the benzene nitration is started up has the further advantage that the hydraulic load in the reaction is lower and therefore the reaction can be ramped up to target load more quickly.

Thus, the process according to the invention, by using sulfuric acid (a.2) with a content of organic compounds of less than 1.0 mass percent, preferably of less than 0.50 mass percent and particularly preferably of less than 0.20 mass percent, based in each case on the total mass of (a.2), allows a technically trouble-free start-up of the adiabatic nitration of benzene and subsequent work-up of the resulting crude nitrobenzene devoid of shutdown periods, the quality of end product being immediately high. After the start-up period, maintenance of these upper limits for the content of organic compounds is no longer essential, although nevertheless advantageous.

EXAMPLES

Contents in ppm or % are proportions by mass, based on the total mass of the respective substance (stream). Analytical values were determined by gas chromatography unless otherwise specified.

General Conditions for the Production of Nitrobenzene in a Production Plant which has been Run in (after the Start-Up Period t has Elapsed)
(Cf. FIG. 1)

A sulfuric acid stream (11), a nitric acid stream (12), a fresh benzene stream (13) and a recycle benzene stream (21) are fed into a reactor (1). The benzene is used in 5 to 10% excess, based on nitric acid. The amount of recycle benzene obtained depends on this excess and the quality of the starting benzene. Once all the nitric acid has reacted with the benzene to give nitrobenzene under adiabatic reaction conditions, the reaction product (14), now at a temperature of approx. 130° C., is fed into a phase separation apparatus (2), in which the reaction product (14) separates into an organic phase ((15)=crude nitrobenzene, comprising benzene and low boilers in addition to nitrobenzene) and an aqueous phase ((16)=waste acid, still comprising small proportions of nitrobenzene and benzene in addition to sulfuric acid). The aqueous phase (16), comprising mainly sulfuric acid, is subjected to a flash evaporation of water in the evaporator (3) by sudden pressure reduction, and is thereby concentrated. The concentrated sulfuric acid (17) is stored in the sulfuric acid tank (4) until it is re-used. After separation in the phase separation apparatus, the crude nitrobenzene (15) is cooled to approx. 50° C. in the crude nitrobenzene cooler (5) and fed into the wash (6). The resulting stream of purified crude nitrobenzene (18), substantially freed of nitrophenols and salts, is heated again and, in a distillation column (7), freed of water, benzene and other low boilers, which are separated off (19) overhead, to give dried pure nitrobenzene (20), which is stored in a tank (8). The condensed head product (19) of the distillation column (7) is fed into a phase separation apparatus (9), in which the head product separates into an organic phase ((21), comprising benzene and low boilers) and an aqueous phase (22). The organic phase (21) is temporarily stored in a buffer tank (10) and from there, as already described above, is returned into the inlet of the reactor (1) for reaction. Nitrobenzene prepared in this way typically has a purity of approx. 99.96% (GC), a residual benzene content of 0.0028% (GC), a 1,3-dinitrobenzene content of 0.0273% (GC) and a nitrophenole content of <5 ppm (HPLC). Furthermore, the nitrobenzene has a water content of 0.0079% (Karl-Fischer).

General Conditions for the Start-Up of an Adiabatic Nitrobenzene Process
(Cf. FIG. 1)

The sulfuric acid circulating pump is started up and sulfuric acid from the sulfuric acid tank (4) is fed into the reactor (1) and then runs over into the phase separation apparatus (2) and from there into the evaporation apparatus (3), finally returning to the sulfuric acid tank (4). The pressure in the evaporation apparatus is reduced. When the plant is run hot with sulfuric acid, to ensure careful treatment of the metallic sulfuric acid circulating pumps used in the nitration reaction, traces of nitric acid are always added to the sulfuric acid in order to passivate the sulfuric acid circulating pump and prevent it from being destroyed by corrosion. This is not necessary if plastic pumps are used. In continuous mode of operation, the sulfuric acid is heated with indirect steam to a temperature of 101° C. During heating, the sulfuric acid is circulated through the sulfuric acid tank, the reactor, the phase separation apparatus and the evaporation apparatus, the absolute pressure in the evaporation apparatus being 85 mbar. As soon as the circulating sulfuric acid has reached the target temperature and (examples 2 to 4) the content of organic compounds in the circulating sulfuric acid is according to the invention, the nitration is started up. In comparative example 1 the requirement regarding the content of organic compounds in the circulation sulfuric acid was not met (content of organic compounds higher than 1.0 mass percent). To start up the nitration, a benzene stream (of 13 (fresh benzene) and optionally 21 (recycle benzene)) as well as the nitric acid stream (12) are simultaneously fed to the reactor inlet, where the nitration begins with the dispersion of the starting materials. To reach the target capacity of the plant ($M'_{target}$), the process is initially started with smaller mass flows of benzene and nitric acid (in examples 1 to 4 the plant was started with 50% of the target capacity, corresponding to a production output of 30 t/h (nitrobenzene)). These mass flows are then increased to the target load over a start-up period t. The plant can be brought to target load manually or by means of an automatic start-up program. The plant was always ramped up to target load as quickly as possible, ensuring that complete conversion of the nitric acid was achieved.

TABLE 1

Comparison of the results of the Examples

| Example | Nitrobenzene content of stream 11[a] | Dinitrobenzene content of stream 15[a] | Picric acid content of stream 15[a] |
| --- | --- | --- | --- |
| 1 (comparative) | 1.3 mass percent | 310 ppm | 321 ppm |
| 2 (according to the invention) | 0.95 mass percent | 251 ppm | 240 ppm |
| 3 (according to the invention) | 0.45 mass percent | 195 ppm | 132 ppm |
| 4 (according to the invention) | 0.21 mass percent | 187 ppm | 127 ppm |

[a]mean values over the start-up period

As shown by the examples, large amounts of by-products are formed when the nitrobenzene content of the circulating sulfuric acid is high (example 1). With the strategy according to the invention, on the other hand, the formation of by-products is significantly reduced and subsequent blending of the starting material with purer batches of nitrobenzene can be omitted.

The invention claimed is:

1. A continuous process for the preparation of nitrobenzene by the nitration of benzene, comprising:
   a) reacting a benzene-containing stream (a.1) in a reactor with a mixture of sulfuric acid (a.2) and nitric acid (a.3) under adiabatic conditions, wherein the benzene is used in a stoichiometric excess, based on nitric acid (a.3), and the quantity M' of the benzene-containing stream (a.1) fed into the reactor per hour is increased over a period of time t from the beginning of the nitration until a preset target value for M' is achieved,
   b) separating the process product obtained in step a) in a phase separation apparatus into an aqueous phase (b.1) comprising sulfuric acid and an organic phase (b.2) comprising nitrobenzene,
   c) concentrating the aqueous phase (b.1) obtained in step b) by evaporation of the water in an evaporation apparatus to give an aqueous phase (c.1) comprising sulfuric acid and having a higher sulfuric acid concentration than (b.1), wherein the phase (c.1) is recycled into step a) via a sulfuric acid tank and used as a component of (a.2), and
   d) working up the organic phase (b.2) obtained in step b) to pure nitrobenzene (d.1),
   wherein at least during the period of time t, only a sulfuric acid stream (a.2) having a content of organic compounds of less than 1.0 mass percent, based on the total mass of (a.2), is fed into the reactor.

2. The process according to claim 1 wherein the organic compounds are selected from the group consisting of benzene, nitrobenzene, the isomers of dinitrobenzene and the isomers of nitrophenol.

3. The process according to claim 2 wherein the organic compound comprises nitrobenzene.

4. The process according to claim 1 wherein the continuous reaction is interrupted by stopping the addition of the benzene-containing stream (a.1) and nitric acid (a.3) and, after complete conversion to nitrobenzene of the residual nitric acid present in the reactor, after removal of the organic phase (b.2) from the phase separation apparatus and after concentrating (b.1) to (c.1), the remaining sulfuric acid-containing phase (c.1) is circulated through the reactor, the phase separation apparatus, the evaporation apparatus and the sulfuric acid tank at a temperature of 60° C. to 140° C. until the content of organic compounds in (c.1) is lower than 1.0 mass percent, based on the total mass of the sulfuric acid-containing phase (c.1), and wherein the so purified sulfuric acid-containing phase (c.1) is used as a component of (a.2) in the next production cycle.

5. The process according to claim 1 wherein, starting from a production plant that is not in operation, before the introduction of the benzene-containing stream (a.1) and nitric acid (a.3), the sulfuric acid-containing phase (c.1) which is still present from the previous production cycle is circulated through the reactor, the phase separation apparatus, the evaporation apparatus and the sulfuric acid tank at a temperature of 60° C. to 140° C. until the content of organic compounds in (c.1) is lower than 1.0 mass percent, based on the total mass of the sulfuric acid-containing phase (c.1), and wherein the so purified sulfuric acid-containing phase (c.1) is used as a component of (a.2) in the next production cycle.

6. The process according to claim 4 wherein the absolute pressure in the evaporation apparatus is adjusted to 50 mbar to 300 mbar, while the sulfuric acid-containing phase (c.1) is circulated, in order to bring the content of organic compounds in (c.1) to a value of less than 1.0 mass percent, based on the total mass of the sulfuric acid-containing phase (c.1).

7. The process according to claim 1 wherein benzene is used in step a) in an excess of 2.0% to 20% of theory.

8. The process according to claim 5, wherein the absolute pressure in the evaporation apparatus is adjusted to 50 mbar to 300 mbar, while the sulfuric acid-containing phase (c.1) is circulated, in order to bring the content of organic compounds in (c.1) to a value of less than 1.0 mass percent, based on the total mass of the sulfuric acid-containing phase (c.1).

9. The process according to claim 2, wherein benzene is used in step a) in an excess of 2.0% to 20% of theory.

10. The process according to claim 3, wherein benzene is used in step a) in an excess of 2.0% to 20% of theory.

11. The process according to claim 4, wherein benzene is used in step a) in an excess of 2.0% to 20% of theory.

12. The process according to claim 5, wherein benzene is used in step a) in an excess of 2.0% to 20% of theory.

13. The process according to claim 6, wherein benzene is used in step a) in an excess of 2.0% to 20% of theory.

14. The process according to claim 8, wherein benzene is used in step a) in an excess of 2.0% to 20% of theory.

* * * * *